United States Patent [19]

Schofield et al.

[11] Patent Number: 4,927,759
[45] Date of Patent: May 22, 1990

[54] **NEW STRAINS OF *PSEUDOMONAS PUTIDA* AND THEIR USE**

[75] Inventors: John A. Schofield; Peter R. Betteridge; George Ryback, all of Sittingbourne; Philip J. Geary, Ashford, all of England

[73] Assignee: Shell Oil Company, Houston, Tex.

[21] Appl. No.: 363,575

[22] Filed: Jun. 8, 1989

Related U.S. Application Data

[62] Division of Ser. No. 68,493, Jul. 1, 1987, Pat. No. 4,876,200.

[30] Foreign Application Priority Data

Jul. 8, 1986 [GB] United Kingdom ............... 8616612
Jul. 8, 1986 [GB] United Kingdom ............... 8616613

[51] Int. Cl.$^5$ .................. C12F 7/02; C12P 7/22; C12R 1/40
[52] U.S. Cl. ................... 435/156; 435/155; 435/253.3; 435/877
[58] Field of Search ............ 435/156, 155, 253.3, 435/877

[56] References Cited

U.S. PATENT DOCUMENTS

| | | | |
|---|---|---|---|
| 4,508,822 | 4/1985 | Taylor | 435/155 |
| 4,532,209 | 7/1985 | Hagedorn | 435/156 |
| 4,535,059 | 8/1985 | Hsieh et al. | 435/142 |
| 4,556,638 | 12/1985 | Pillis et al. | 435/253 |
| 4,584,274 | 4/1986 | Sustow | 435/253 |
| 4,876,200 | 10/1989 | Schofield et al. | 435/253.3 |

FOREIGN PATENT DOCUMENTS 76606 4/1983 European Pat. Off. .

OTHER PUBLICATIONS

Gibson et al., *Biochemistry*, 7(7), 1968, p. 2653.
Gibson et al., *Biochemistry*, 9(7), 1970, p. 1631.
Gibson et al., *Biochemistry*, 7(11), 1978, p. 3795.

*Primary Examiner*—Herbert J. Lilling

[57] ABSTRACT

Strains of *Pseudomonas putida* selected from *Pseudomonas putida* NCIB 12190 and mutant strains thereof, which mutant strains can be obtained by chemical and physical mutation, allowing the mutated bacteria to grow prior to exposure to benzene or fluorobenzene, and subsequently, after further growth in the presence of benzene or fluorobenzene, selecting those mutant strains which accumulate cis-dihydroxycyclohexadiene or catechol or their fluorinated analogues. The new strains can be used in biochemical processes for the preparation of cis-dihydroxycyclohexadienes and catechols.

4 Claims, No Drawings

NEW STRAINS OF *PSEUDOMONAS PUTIDA* AND THEIR USE

This is a division of application Ser. No. 068,493 filed July 1, 1987, now U.S. Pat. No. 4,876,200.

This invention relates to new strains of *Pseudomonas putida* and the use of these strains in selective biochemical processes for the production of dihydroxycyclohexadienes and catechols from benzene and certain derivatives thereof.

The ability of the organism *Pseudomonas putida* to metabolise benzene and certain substituted benzenes to their corresponding catechols and further degradation products is known from the work of Gibson et al, Biochemistry, 7(7), 1968, p. 2653; and Biochemistry, 9(7), 1970, p. 1631. Thus, the metabolism is believed to follow the following enzyme catalysed reaction sequence:

[Chemical scheme: (I) benzene with R substituent → (II) cis-dihydroxycyclohexa-3,5-diene with R, OH, OH → (III) catechol with R, OH, OH]

In accordance with this metabolic pathway, benzene (I; R=H) is converted by a dioxygenase to cis-1,2-dihydroxycyclohexa-3,5-diene (II; R=H) (sometimes known as "cis-benzene glycol" or "benzene dihydrodiol") which under the action of a diol dehydrogenase is converted to catechol (III; R=H) which is enzymatically converted to further degradation products. A related pathway, where R is methyl, is believed to occur for toluene metabolism using *Pseudomonas putida* (Gibson et al, Biochemistry, 9(7), 1970, p. 1627).

While compounds of formulae (II) and (III) would be useful products or intermediates to obtain by a biochemical process, it has been found difficult to control the reaction to give sufficient yield of the desired product without contamination by the other metabolic products. Attempts to produce, for example, a compound of formula (III) from both wild type and mutant strains of *P.putida* have relied on the need to induce the required enzymes for the conversion reactions using benzene or toluene as carbon source. Thus Gibson et al, (Biochemistry 7(11), 1978, p. 3795) used toluene as carbon source when carrying out investigations on the ability of *P.putida* to oxidise halogenated benzenes, while Taylor (European Patent No. 0076606) likewise employed toluene to induce the required enzymes in his preparation of compounds of formula (II) from certain mutant strains of *P.putida*. Such induction procedures are disadvantageous as the introduction of another carbon source for induction purposes contaminates the reaction mixture and necessitates complex separation problems before a pure product can be obtained.

Taylor (European Patent No. 0076606) was able to obtain certain dihydroxycyclohexadienes without induction by further mutating a certain mutant strain of *Pseudomonas putida*. The separation of these second mutants was made by a selection procedure which involved spraying with catechol and selecting colonies which gave a colour reaction indicative of the conversion of catechol into 2-hydroxymuconic semialdehyde, i.e. a ring fission between positions 2 and 3 of the catechol ring, whereas an alternative metabolic pathway involves fission between the 1 and 2 positions of the catechol ring to give a muconic acid.

We have now found a wild type strain of *Pseudomonas putida* which is constitutive of the necessary enzymes in the preparation of certain catechols of formula (III). In other words, we have found a strain in which the necessary enzymes do not have to be induced. This strain is that deposited with effect from 6th December 1985 with the National Collection of Industrial Bacteria, Torry Research Station, Aberdeen, Scotland and assigned the numerical designation NCIB 12190 and referred to herein as ""*P.putida*" NCIB 12190".

*Pseudomonas putida* NCIB 12190 has been characterised and identified by the NCIB as follows:

Tests were at 25° C. and growth was on LAB M Nutrient Agar unless otherwise stated.

Cell Morphology

After growth for 24 hours at 30° C. on succinate agar and transfer to Nutrient broth+0.75% w. agar, by phase contrast at ×630 magnification the cells are small short rods or cocci in clusters.

Gram Negative
Spores—
Motility+

Colonial Morphology

After 48 hours growth, colonies are round, regular, entire, smooth, opaque, low convex, off-white and less than 1 mm in diameter.

Growth on Glucose Peptone Water Sugars
37° C.+
41° C.—
Catalase+
Oxidase, Kovacs+
O-F glucose Oxidative "O-F glucose" was performed using the oxidation-fermentation medium of Hayward and Hodgkiss, *J. Gen. Microbiol.*, 26, (1961), pp. 133–140, supplemented with 1% w. filter-sterilised D-glucose. A tube sample was inoculated and incubated for 14 days.

*Pseudomonas putida* NCIB 12190 can conveniently be stored on nutrient agar slopes at 4° C., or as a freeze-dried material.

The UV mutant of *Pseudomonas putida* NCIB 12190 described in Example 1 had the same characteristics as those described above, exception of motility-negative.

*P.putida* NCIB 12190 was isolated from a soil sample taken from ground within the Shell Refinery at Pernis, Rotterdam.

We have further found that mutants can be obtained directly from *Pseudomonas putida* NCIB 12190, which mutant strains can be used to catalyse the reactions of the above described reaction sequence without the need for enzyme induction. Furthermore, we have found that certain mutants catalyse preferentially the conversion of (I) to (II), thus maximizing the yield of the cis-dihydroxycyclohexadiene and suppressing the later reactions in the sequence, while other mutants catalyse the conversion from (I) through to (III), but not the conversion to further degradation products. Therefore the reaction can be tailored by use of the appropriate mutant to give the desired product of formula (II) or (III).

According to this invention we provide strains of *Pseudomonas putida* selected from *Pseudomonas putida* NCIB 12190 and mutant strains thereof, which mutant strains are capable of accumulating cis-dihydroxycyclohexadiene or catechol or their fluorinated analogues when cultured in the presence of benzene or fluorobenzene and are obtainable by a selection procedure which comprises mutating *Pseudomonas putida* NCIB 12190 by chemical or physical means, allowing the mutated bacteria to grow in the presence of a carbon source, exposing the grown bacteria to benzene or fluorobenzene and selecting those mutant strains which have accumulated cis-dihydroxycyclohexadiene or catechol or their fluorinated analogues.

The mutation may be carried out by chemical means, employing, for example, as mutating agent N-methyl-N'-nitro-N-nitrosoguanidine (referred to hereinafter as ("NTG")). Other mutating agents may be employed, such as 2-aminopurine or 5-bromouracil. The mutation may also be carried out by physical means for example by ultraviolet irradiation or using other ionizing radiation methods.

Examples of preferred carbon sources are succinic acid and fumaric acid, suitably in the form of salts such as disodium succinate and disodium fumarate. Other suitable carbon sources include sucrose, galactose, lactose, citrates, fructose and glycerol.

An alternative preferred carbon source has been shown to be molasses, both in the form of sugar cane molasses, commerically available as "black strap molasses", and in the form of beet molasses.

The nutrient medium may be any suitable medium for the growth of the mutant strains, an example being a minimal salts medium containing sodium succinate.

Preferred strains of *Pseudomonas putida* are mutant strains. Particularly preferred mutant strains are those designated NTG-mutant F and UV-mutants A and B, described hereinafter.

The invention further includes the use of the new mutant strains in biochemical processes for the production of cis-dihydroxycyclohexadienes and catechols.

Therefore according to a further aspect of this invention we provide a biochemical process for the preparation of a compound of formula (II):

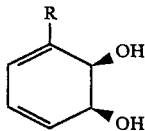 (II)

from a compound of formula (I)

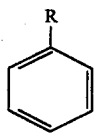 (I)

wherein R is hydrogen or fluorine, comprising providing a culture of a mutant strain of *P.putida* which accumulates cis-dihydroxycyclohexadiene or its fluorinated analogue in the selection procedure defined above, supplying a compound of formula (I) to the culture in a suitable medium and subsequently recovering a compound of formula (II) therefrom.

According to an alternative aspect of this invention we provide a biochemical process for the preparation of a compound of formula (III)

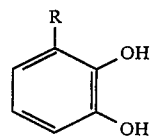 (III)

from a compound of formula (I)

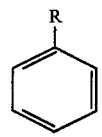 (I)

wherein R is hydrogen, or fluorine, comprising providing a culture of *P.putida* NCIB 12190 or a mutant strain thereof which accumulates catechol or 3-fluorocatechol in the selection procedure defined above, supplying a compound of formula (I) to the culture in a suitable medium and subsequently recovering a compound of formula (III) therefrom.

A preferred medium for the production of the compounds of formulae (II) and (III) comprises sodium succinate as carbon source, for example in combination with ammonium sulphate. Other suitable carbon sources include fumarates, frutose, glycerol, sucrose, galactose, lactose and citrates. A further preferred carbon source is molasses, in the form of sugar cane molasses or beet molasses. The use of molasses as carbon source in the biochemical production of cis-dihydroxycyclohexadienes and catechols from the corresponding benzenes is the subject of our co-pending application Ser. No. 068,491, allowed.

If desired a protein synthesis inhibitor such as chloramphenicol may be included in the process for preparing compounds (II) or (III) to enhance accumulation of the desired products.

The desired product compound may be recovered from the resulting fermentation broth by any suitable means such as absorption onto granulated charcoal followed by stripping with a suitable solvent, or solvent extraction.

While the starting material of formula (I) may be benzene, a preferred starting material is fluorobenzene, giving as products 3-fluoro-cis-1,2-dihydroxycyclohexa-3,5-diene (II: R=F) and 3-fluorocatechol (III; R=F). The former can be readily used as an intermediate in its own right or can be converted by chemical means to 3-fluorocatechol, 2-fluorophenol or 3-fluorophenol. 3-Fluorocatechol is difficult to prepare by purely chemical means and is expensive. It is a useful intermediate in the production of, for example, pharmaceuticals and organo-fluorine agrochemicals.

Examples of preferred mutants for the preparation of 3-fluorocatechol are those described hereinafter and designated UV-mutant A, and UV-mutant B which can be obtained by UV mutagenesis followed by exposure of the mutant organism to fluorobenzene.

The invention will now be described further by way of example.

Colorimetric determination of
Cis-dihydroxycyclohexadienes and catechols.

The methods of Friestad et al., Analytical Chemistry 41, 1969, pp. 1750–1754 was used. Solutions to be tested for catechols were mixed with an equal volume of 3- methyl-2-benzothiazolinone hydrazone hydrochloride (0.05% w/v in water) and an equal volume of ceric ammonium sulphate (0.2% w/v in 0.4% w/v sulphuric acid). Optionally, a borate-NaOH-EDTA buffer was added after a few minutes, as described by Friestad et al. The intensities of the colours which developed were compared visually or, alternatively, were measured spectrophotometrically at 520 nm. Cis-dihydroxycylohexadienes do not produce colours under these conditions. Therefore a second sample of each test solution was acidified with sulphuric or hydrochloric acid before the colour test, to convert the dihydroxycyclohexadienes quantitatively to phenols. The difference in colour intensity given by the acidified and unacidified samples is indicative of the content of dihydroxycyclohexadienes.

Media Used

The compositions of two of the media used in the following examples are given below in Table 1.
ASM - minimal salts medium
NFSM - nitrogen-free salts medium

TABLE 1

|  | amounts per liter | |
| --- | --- | --- |
|  | ASM | NFSM |
| $Na_2HPO_4$ | 0.866 g | 7 g |
| $KH_2PO_4$ | 0.531 g | 3 g |
| $NH_4Cl$ | 0.535 g | — |
| $K_2SO_4$ | 0.174 g | 0.174 g |
| $MgSO_4.7H_2O$ | 0.037 g | 0.037 g |
| $CaCl_2.2H_2O$ | 0.00735 g | 0.00735 g |
| TK3 (T/E) (see below) | 1.0 ml | 1.0 ml |
| $FeSO_4.7H_2O$ (0.1 M) | 0.2 ml | 0.2 ml |
|  | pH 6.8 | |

Composition of TK/3 Trace Element Solution:

This contained per liter the following components: $ZnSO_4.7H_2O$ (0.288 g); $MnSO_4.4H_2O$ (0.224 g); $H_3BO_3$ (0.0618 g); $CuSO_4.5H_2O$ (0.1248 g); $Na_2MoO_4.2H_2O$ (0.0484 g); $CoCl_2.6H_2O$ (0.0476 g); KI (0.083 g); 1M $H_2SO_4$ (1 ml).

| Further media used were: | |
| --- | --- |
| dYT medium | 16 g Bacto tryptone |
|  | 10 g Bacto yeast extract |
|  | 5 g NaCl/l |
| Yeast extract medium (YEM) | 10 g/l disodium succinate .6H$_2$O |
|  | 2 g/l (NH$_4$)$_2$SO$_4$ |
|  | 3 g/l yeast extract (Difco) |
|  | 0.4 g/l MgSO$_4$.7H$_2$O |
|  | 0.04 g/l Bacto-peptone in |
|  | 25 mM potassium phosphate |
|  | buffer, final pH 7.0. |

Thin layer chromatography (TLC)

Aqueous samples (5 μl) were run on Merck Kieselgel 60 F254 plates developed with 90:10:1 (v/v) n-propanol-water-formic acid. Dihydroxycyclohexadiene content was visualised under short wave uv light and catechol was detected by spraying with 2,6-dichloroquinone-4-chloroimide (2% in ethanol).

Gas chromatography (GC).

Aqueous samples (0.5 μl) were chromatographed on a Hewlett Packard 25-meter high capacity flexible silica capillary column coated with 5%-phenylmethylsilicone, using helium as carrier gas. The column was held at 130° C., and eluted compounds were detected by a flame ionisation detector.

EXAMPLE 1

The preparation of NTG mutants of P.putida NCIB 12190

*Pseudomonas putida* NCIB 12190 was grown overnight at 30° C. in dYT medium. The culture was subcultured 1/20 into 10 ml fresh dYT and incubated for a further 4 hours. The bacteria were harvested by centrifugation, washed in NFSM and again harvested by centrifugation before resuspension in NFSM (3 ml) and adjustment of the OD 600 nm to 3.0.

A 1 ml aliquot in an "Eppendorf" tube was incubated at 30° C. for 15 mins and then NTG (N-methyl-N'-nitro-N-nitrosoguanidine-5mg/ml in dimethyl sulphoxide) added to give 50 μg/ml. The tube contents were briefly mixed and incubated at 30° C. for 15 mins. Mutation was stopped by chilling in ice, centrifugation and washing (3 times in saline-0.85% NaCl). The bacteria were diluted in saline and 0.1 ml aliquots plated out onto 100 ASM plates each including 0.05% sodium succinate. The plates were incubated at 30° for 48 hours.

After incubation, small "micro" colonies were visible on the plates, the level of succinate having been only sufficient for a small amount of growth. The plates were then exposed to benzene vapour for 24 h at 30° C. resulting in a wide variety of colony sizes visible on the plates. In an initial selection procedure, small colonies on the plates (which are small because of their inability to grow on benzene) (20–30/plate) were picked using sterile cocktail sticks into 96 well microtitre plates (Titertek) containing 50 μl ASM+0.5% sodium succinate per well. The plates were incubated overnight at 30° C. in a sealed box to prevent evaporation and the microtitre plates replicated onto square (120 mm) plates of commercial nutrient agar (Oxoid) (to provide controls) using a 96 prong replicating device. The agar plates were incubated overnight and the microtitre plates were exposed to benzene vapour for 3 hours. Subsequent assay was by the colorimetric method described above. Those mutants developing the most intense colour were selected for further testing for the accumulation of catechol an cis-dihydroxycyclohexadiene and identification of the best mutants for production of each. The selected best mutants were tested using shake flask cultures and the colorimetric determination again carried out. Controls were run using a culture of wild type *P.putida* NCIB 12190 to which chloramphenicol had been added as a protein synthesis inhibitor, although no chloramphenicol was added to the mutant strains. Confirmatory HPLC analyses of some of the supernatants were carried out.

From each of six independent starting cultures of *P.putida* NCIB 12190 mutated with NTG, 100 plates were innoculated giving approximately 100,000 colonies, 13,500 of which were picked into microtitre plates and 435 initially selected for colour testing. 90 of these were further investigated after colour testing and TLC analysis and shake flask experiments carried out on 14 of the mutants.

The cultures were grown overnight in ASM plus 0.5% sodium succinate, harvested by centrifugation, washed and resuspended in NFSM. The cultures were exposed to benzene and the supernatants assayed for catechol or catechol plus cis-dihydroxycyclo- hexadiene. For control runs, wild type *P.putida* NCIB 12190 was employed with chloramphenicol (1 mg/ml) added to the NFSM medium.

Catechol producing mutants

Several mutants produced amounts of catechol at least comparable to those produced by a control using wild type *P.putida* NCIB 12190 plus chloramphenicol, even though the mutants did not need the presence of chloramphenicol.

These mutants are hereinafter referred to as "NTG-mutants A, B, C and D". The results for mutants B, C and D are shown in Table 2.

TABLE 2

| Strain | OD 520 nm. after 3 hrs | after 7 hrs |
|---|---|---|
| Mutant B | 0.25 | 0.49 |
| Mutant C | 0.21 | 0.47 |
| Mutant D | 0.34 | 0.58 |
| NCIB 12190 + chloramphenicol | 0.23 | 0.47 |

Cis-dihydroxycyclohexadiene producing mutants

Two mutants were unable to produce catechol but accumulated cis-dihydroxycyclohexadiene. These mutants are hereinafter referred to as "NTG-mutants E and F". The results for mutants E and F are shown in Table 3.

TABLE 3

| | OD 520 nm | | | |
|---|---|---|---|---|
| | Catechol | | Catechol plus cis-dihydroxycyclohexadiene | |
| Strain | after 2½ hrs | after 7 hrs | after 2½ hrs | after 7 hrs |
| Mutant E | 0.02 | 0.02 | 0.17 | 0.24 |
| Mutant F | 0.04 | 0.06 | 0.27 | 0.54 |

The advantageous effect on diene production of the addition of a protein synthesis inhibitor (chloramphenicol-1 mg/ml) to mutants E and F is shown in Table 4.

TABLE 4

| Strain | OD 520 nm Catechol plus cis-dihydroxycyclohexadiene | |
|---|---|---|
| | after 2½ hr | after 7 hr |
| Mutant E | 0.17 | 0.24 |
| Mutant E plus chloramphenicol | 0.49 | 0.75 |
| Mutant F | 0.27 | 0.54 |
| Mutant F plus chloramphenicol | 0.34 | 0.85 |

EXAMPLE 2

The production of NTG mutants of *P.putida*.

Example 1 was repeated as far as the initial selection procedure and 450 candidate organisms from the initial selection procedure were received as purified cultures on agar plates and inoculated into 1.5 ml of an ASM medium (supplemented with a trace element mixture, $Fe^{2+}$ —20 μm and sodium succinate -5 g/l). The cultures were grown overnight in sloping rotating test tubes at 30° C., centrifuged, the supernatants discarded and the cells resuspended in 0.25 ml supplemented ASM in test tubes arranged nearly horizontally in a tank of benzene vapor on a rocking platform at room temperature.

After a certain benzene exposure time (usually 3 and/or 5 to 6 hours) two 0.5 ml samples of each culture were withdrawn for colour testing by the colorimetric method described above. To one of these were added 10 μl of 5M HCl to convert any cis-dihydroxycyclohexadiene present into phenol. 5 μl samples were also taken for TLC analysis. After the benzene exposure, the cultures were left in air and a final TLC sample taken next day.

Two cultures of wild type *P.putida* NCIB 12190 were included in each batch tested for comparison purposes, to one of which chloramphenicol (0.1 mg/ml) had been added before exposure to benzene. Colours and TLC spots were compared and scored on an eight-point scale from —to +++. The results are given in Table 5. Reproducability was found to be good.

TABLE 5

| | 3 hr benzene exposure | | | | 5-6 hr benzene exposure | | | |
|---|---|---|---|---|---|---|---|---|
| | Colour Test | | TLC | | Colour Test | | TLC (next day) | |
| Mutant | + acid | no acid | Diene | Catechol | + acid | no acid | Diene | Catechol |
| CONTROLS | | | | | | | | |
| NCIB 12190 | +(+) | +(+) | — | +(+) | ++ | ++ | — | + |
| NCIB 12190 + chloramphenicol | +++ | +++ | — | +++ | +++ | +++ | — | +++ |
| CIS-DIHYDROXY-CYCLOHEXADIENE PRODUCERS | | | | | | | | |
| NTG mutant E | (+) | — | — | — | —(+) | — | (+) | — |
| NTG mutant G | (+) | —(+) | (+) | — | (+) | —(+) | — | — |
| NTG mutant H | + | —(+) | (+) | — | + | —(+) | (+) | — |
| NTG mutant F | +(+) | —(+) | + | — | + | —(+) | + | — |
| NTG mutant I | —(+) | — | — | — | —(+) | — | — | — |
| NTG mutant J | (+) | —(+) | — | — | (+) | —(+) | — | — |
| NTG mutant K | ++ | | | | ++ | (+) | — | (+) |
| NTG mutant L | —(+) | — | — | — | —(+) | — | — | — |
| NTG mutant M | (+) | — | — | —(+) | + | (+) | — | — |
| CATECHOL PRODUCERS | | | | | | | | |
| NTG mutant C | ++ | | | | ++ | +++ | — | +++ |
| NTG mutant N | +++ | +++ | — | +++ | ++(+) | ++(+) | — | +++ |
| NTG mutant O | +++ | ++(—) | — | +++ | ++(+) | ++(+) | — | +++ |
| NTG mutant P | +++ | ++(—) | — | ++(+) | ++(+) | ++(+) | — | +++ |
| NTG mutant Q | ++(+) | ++(—) | — | ++(+) | ++(+) | ++(+) | — | ++(+) |
| NTG mutant A | ++ | ++ | — | +++ | ++ | ++ | — | +++ |
| NTG mutant R | +++ | +++ | — | +++ | +++ | +++ | — | ++(+) |
| NTG mutant S | | | | | ++ | ++(+) | — | ++(+) |

TABLE 5-continued

| | 3 hr benzene exposure | | | | 5-6 hr benzene exposure | | | |
| | Colour Test | | TLC | | Colour Test | | TLC (next day) | |
| Mutant | + acid | no acid | Diene | Catechol | + acid | no acid | Diene | Catechol |
| --- | --- | --- | --- | --- | --- | --- | --- | --- |
| NTG mutant R | | | | | ++ | ++ | — | ++(+) |
| NTG mutant U | | | | | ++ | ++ | — | ++(+) |
| NTG mutant V | | | | | ++ | ++(+) | — | +++ |

EXAMPLE 4

The use of NTG Mutant F in the production of 3-fluoro-cis-1,2-dihydroxycyclohexa-3,5-diene using succinate as carbon source.

8 Liters of YEM were inoculated in a stirred fermenter with a 20 hour shake flask culture of NTG Mutant F grown on the same medium (50 ml). The organism was grown at aerating conditions of 500 rpm and 500 ml. air/min. for 19 hours with a continuous feed of concentrated nutrient (320 g of disodium succinate and 64 g of ammonium sulphate in 1 liter of 0.025M potassium phosphate buffer pH 7.2) at 40 ml/hour. Oxygen transfer was increased by increasing the stirrer speed to 550 rpm and the aeration rate to 700 ml air/min for 30 min and then set to conditions of 500 rpm; 600 ml air/min; equilibrium oxygen tension 30% air saturated initially).

Fluorobenzene was metered by a pump (Gilson Model 302) at 50 μl/min (100–125 mg/l equilibrium concentration in the reaction). Prior to reaction, the optical density was determined as 3.11 corresponding to a dry cell weight of 3.9 g/l. Production of 3-fluoro-cis-1,2-dihydroxycyclohexa-3,5-diene (II; R=F) was monitored by gas chromatography and the concentration reached 2.8 g/l after 24 hr.

The product was absorbed on granulated charcoal and recovered from the charcoal by extraction in a Soxhlet apparatus with a mixture of diethyl ether and methanol (4:1 v/v). Evaporation of the solvent left a solid which was recrystallised from a mixture of diethyl ether and pentane to give colourless needles, m.p. 73–74° C. (decomp.).

UV Spectrum ($H_2O$): λ max 259 nm (Σ3150).

Circular dichroism) ($H_2O$: λ max 255 nm (ΔΣ −1.9).

Mass spectrum m/z 130 (15%,$M^+$), 112 (65%), 84 (100%).

$^1$H-NMR spectrum ($CDCl_3$): δ5.88 (1H, mult, J=10, 6.5, 6, 2 Hz; 5—C—H), 5.71 (1H, dd, J=10, 3 Hz; 6—C—H), 5.60 (1H, dd, J=11, 6.5 Hz; 4—C—H), 4.51 (1H, br.mult, J=6, 3, 2 Hz; 1—C—H), 4.29 (1H, tr, J=6, 6 Hz; 2—C—H), 2.40 (2H, br.s, O—H) p.p.m.

EXAMPLE 5

The use of NTG mutant F in the production of 3-fluoro-cis-1,2-dihydroxycyclohexa-3,5-diene using molasses as carbon source A medium of 25 mM phosphate buffer (pH 7.0; 8 l) containing cane molasses (240 g), yeast extract (24 g), ammonium sulphate (16 g), magnesium sulphate heptahydrate (3.2 g) and bactopeptone (0.32 g) was inoculated with a shake flask culture of NTG mutant F and air was passed at a rate of 500 ml/min into the stirred mixture (500 rpm) over a period of 20 hours. During the latter 16 hours of growth, the fermenter was fed with a solution of cane molasses (500 g/l) and ammonium sulphate (50 g/l) in 25 mM phosphate buffer (pH 7.0) at a rate of 40 ml/hour. The pH of the broth was maintained at about 7.0 by addition via a monitoring system of 10% aqueous sodium hydroxide.

After 20 hours incubation, 5 liters of the broth were withdrawn and the remainder diluted with 25 mM phosphate buffer (pH 7.0; 5l) containing ammonium sulphate (5 g). The mixture was aerated under conditions of 750 ml/min; 600 rpm and fluorobenzene (0.2 ml) added. A solution of cane molasses (250 g/l) and ammonium sulphate (25 g/l) in 25 mM phosphate buffer (pH 7.0) was added at a rate of 40 ml/hour and fluorobenzene was added at a rate of 50 μl/min. Air feed and stirring were adjusted to maintain a positive (about 30%) oxygen tension. After 5 hours, the air feed was raised to 800 ml/min and maintained for a further 15 hours.

The product reached a level of greater than 9 g/l and was isolated from the broth by absorption onto charcoal. Elution of the charcoal with ether/methanol gave product 3-fluoro-cis-1,2-dihydroxycyclohexa-3,5-diene (II; R=F; 46 g), identical with the product of Example 4.

EXAMPLE 6

The preparation of UV mutants of P-putida.

Aliquots of 1 ml of a suspension of P.putida NCIB 12190 in phosphate buffer pH7 were spread onto nutrient agar plates. The plates were irradiated using a chromatolux u.v. lamp for 5 to 30 minutes. The plates were incubated at 30° C. overnight and then placed in an atmosphere of fluorobenzene at 30° C. and incubated for a further 24 hours. 34 surviving colonies were purified and tested for their ability to accumulate fluorocatechol in shake flask experiments. Fluorocatechol was assayed by gas chromatography. In comparative experiments, one mutant strain, hereinafter referred to as as UV-mutant A, accumulated 0.68 g/l fluorocatechol in 3–4 hr, and a second mutant strain, designated UV-mutant B, accumulated 0.56 g/l in 3–4 hr. Under the same conditions the wild strain NCIB 12190 accumulated 0.41 g/l.

EXAMPLE 7

The use of UV mutant A in the production of 3-fluorocatechol

8 Liters of YEM in a fermenter were inoculated with 30 ml of a 16 hour shake culture of UV-mutant A grown at 30° C. on the same medium. The organism was grown under conditions of oxygen limitation (200 rpm, 350 ml air/min) for 17 hours, during which time a zero reading was recorded on the oxygen electrode. After 17 hours the aeration rate was increased to 400 rpm; 450 ml air/min to stimulate growth and maintained for 1 hour to provide an actively growing culture of dry weight 0.6 g/l (viable cell count $1.9 \times 10^9$/ml). Fluorobenzene (10 ml) was added and aeration decreased to 320 rpm; 150 ml air/min. The air was saturated with fluorobenzene by passage through a bubbler containing that compound, maintaining an equilibrium concentration of fluorobenzene of about 300 mg/l in the reaction mixture. 3-Fluorocatechol production was monitored by GLC and estimated to have reached 0.45 g/l after 6 hours and 0.62 g/l after 24 hours. The pH was controlled throughout at 7.2 by automatic addition of $H_2SO_4$.

3-Fluorocatechol (III); R=F was isolated from the culture broth by absorption on charcoal and recovered from the charcoal by solvent extraction, as described in Example 4. After purification by sublimation and recrystallisation from toluene, the product formed colourless platelets, m.p 75.5-72° C.

UV spectrum ($H_2O$): max 267 nm (1060).

Mass spectrum: m/z 128 (100%, M+), 80 (55%), 52 (70%).

$^1$H-NMR spectrum ($CDCl_3$): 6.8-6.65 (3H, mult; Ar—H), 5.72 (1H, br.s; O—H), 5.40 (1H, br.s; O—H) p.p.m.

EXAMPLE 8

The use of *Pseudomonas putida* NCIB 12190 in the production of catechol using succinate as carbon source

*P.putida* NCIB 12190 was grown overnight at 30° C. in ASM using as carbon source disodium succinate. $6H_2O$ (0.5%). After growth the bacteria were harvested by centrifugation, washed and resuspended in NFSM.

The washed and resuspended bacteria were placed into a 250 ml centre well flask. A few drops of benzene were added to the centre well and the flask sealed with "Nescofilm". The flask was incubated without shaking at 30° C.

Samples were taken at time intervals and following each sampling the flask was freshly sealed. Samples of 0.5 ml were withdrawn and the bacteria were removed by centrifugation for 1 min. in an "Eppendorf" bench centrifuge. The presence of catechol was measured by the colorimetric method described above.

The results are shown in Table 6.

TABLE 6

| Strain | OD 520 nm | |
|---|---|---|
| | after 3 hrs | after 7 hrs |
| NCIB 12190 | 0.10 | 0.17 |

EXAMPLE 9

The use of *Pseudomonas putida* NCIB 12190 in the production of catechol using succinate as carbon source and chloramphenicol as protein synthesis inhibitor The process of Example 8 was repeated using disodium succinate. $6H_2O$ as carbon source. In one run chloramphenicol (1 mg/ml) was added to the NFSM in which the bacteria were resuspended after growth. No chloramphenicol was added to the comparison run. Catechol formation was assayed after exposure to benzene as described in Example 8 and the results are shown in Table 7:

TABLE 7

| Strain | OD 520 nm | |
|---|---|---|
| | after 2 hrs | after 5 hrs |
| NCIB 12190 | 0.07 | 0.04 |
| NCIB 12190 plus chloramphenicol | 0.08 | 0.23 |

It will be seen that, although both cultures metabolise benzene immediately, much higher levels of catechol accumulated in the chloramphenicol treated bacteria. Furthermore, there was no evidence of breakdown of catechol in the chloramphenicol treated bacteria. Furthermore, there was no evidence of breakdown of catechol in the chloramphenicol treated cells, while in the untreated cells the amount of catechol decreased after reaching a peak at about 3 hours.

EXAMPLE 10

The use of *Pseudomonas putida* NCIB 12190 in the production of catechol using succinate as carbon source - effect of nitrogen limitation The process of Example 8 was repeated using disodium succinate. $6H_2O$ as carbon source. Four runs were carried out which differed as follows:

Run A: The culture was initially grown in ASM and then resuspended in NFSM without chloramphenicol addition.

Run B: The culture was initially grown in ASM and then resuspended in NFSM with the addition of chloramphenicol (1 mg/ml).

Run C: The culture was initially grown in NFSM including $(NH_4)_2SO_4$ (0.05%) and then resuspended in NFSM without the addition of chloramphenicol.

Run D: The culture was initially grown in NFSM including $(NH_4)_2SO_4$ (0.05%) and then resuspended in NFSM with the addition of chloramphenicol (1 mg/ml).

Runs C and D were thus nitrogen limited cultures containing 10% of the nitrogen present in Runs A and B. Catechol formation was assayed after exposure to benzene as described in Example 8 and the results are shown in Table 8:

TABLE 8

| Run | OD 520 nm | |
|---|---|---|
| | After 3½ hrs | After 6½ hrs |
| A | 0.02 | 0.02 |
| B | 0.33 | 0.61 |
| C | 0.30 | 0.56 |
| D | 0.53 | 1.03 |

The results show that the catechol accumulation was substantially enhanced in the nitrogen limited cultures (Runs C and D) compared with Runs A and B where there was no attempt at nitrogen limitation. The use of chloramphenicol enhanced catechol accumulation over and above the nitrogen limitation (Run D).

EXAMPLE 11

The use of *Pseudomonas putida* NCIB 12190 in the production of catechol using various substances as carbon source, with and without added chloramphenicol The process of Example 8 was repeated using as carbon source the substances listed in Table 9. Carboxylic acids were added as their sodium salts. For each experiment the carbon source, its concentration in the culture medium, and the resulting cell density after growth overnight, estimated from the turbidity of the culture, are given in Table 9. The production of catechol by the resuspended cells, with and without added chloramphenicol (1 mg/ml), was estimated colorimetrically and is shown in Table 9. An increasing number of "+" signs in Table 9 indicates increasing turbidity or intensity of colour.

TABLE 9

| Carbon source | Concentration g/l | Cell density | Catechol Production Without chloramphenicol | With chloramphenicol |
|---|---|---|---|---|
| Succinate | 10 | +++ | ++ | +++ |
| Fructose | 10 | ++ | ++(+) | +++ |
| Sucrose | 4 | ± | ± | ++ |
| Galactose | 10 | + | +(+) | ++ |
| Lactose | 10 | ± | + | ++ |
| Fumarate | 10 | ++ | +(+) | ++(+) |
| Formate | 10 | ± | ± | + |
| Citrate | 10 | ++ | + | +(+) |
| Ethanol | 10 | ± | ± | + |
| Glycerol | 10 | +(+) | + | +++ |

EXAMPLE 12

The use of *Pseudomonas putida* NCIB 12190 in the production of 3-fluorocatechol using succinate as carbon source The process of Example 8 was repeated using disodium succinate. 6H$_2$O as carbon source but employing fluorobenzene as feedstock for addition to the resuspended bacteria in centre well flasks. Two runs (Runs A and B) were carried out using fluorobenzene, which differed in that Run A was carried out without the addition of chloramphenicol, whereas, for Run B, chloramphenicol (1 mg/ml) was added to the NFSM used for resuspension.

For comparison purposes, two runs (Runs C and D) were carried out using benzene which differed in that Run C was carried out without the addition of chloramphenicol, whereas, for Run D, chloramphenicol (1 mg/ml) was added to the NFSM used for resuspension.

Fluorocatechol and catechol formation were assayed as described in Example 8 and the results are shown in Table 10:

TABLE 10

| Run | OD 520 nm After 4 hrs | After 7 hrs |
|---|---|---|
| A | 0.37 | 0.63 |
| B | 0.31 | 0.57 |
| C | 0.31 | 0.53 |
| D | 0.55 | 0.97 |

The results of Runs A and B show that 3-fluorocatechol is formed from fluorobenzene but that the use of chloramphenicol as protein synthesis inhibitor has little effect and, indeed, in this case is slightly disadvantageous.

EXAMPLE 13

The isolation of 3-fluorocatechol from culture broths

3-Fluorocatechol was recovered from culture broths such as those produced by scaled up Run A of Example 12 by centrifugation to remove cells, followed by continuous extraction with diethyl ether for 18 hours. Evaporation of the ether yielded a white solid which was further purified by sublimation (50°–60° C., 10 torr). The product had m.p. 65°–68° C.

Elemental analysis: Found, C 56.7, H 3.5%; Calc. for C$_6$H$_5$FO$_2$, C 56.3; H 3.9%. The ultraviolet absorption spectrum, mass spectrum, and $^1$H- and $^{19}$F-nuclear magnetic resonance spectra agreed with those obtained for a synthetic reference sample.

We claim:

1. A biochemical process for the preparation of a compound of formula (III)

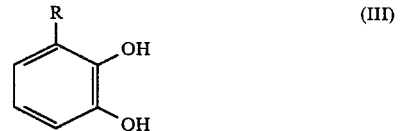
(III)

from a compound of formula (I)

(I)

wherein R is hydrogen or fluorine, comprising providing a culture of a strain of *Pseudomonas putida* NCIB 12190 or mutant thereof, which is constitutive for and which accumulates catechol or 3-fluorocatechol, supplying a compound of formula (I) to the culture in a suitable medium in the absence of an inducing agent for said strain and subsequently recovering a compound of formula (III) therefrom.

2. A process according to claim 1 wherein the mutant strain is UV-mutant A or UV-mutant B.

3. A process according to any one of claims 2 or 1 wherein the medium comprises a material selected from succinates, fructose, fumarates and glycerol.

4. A process according to any one of claims 2 or 1 wherein R is fluorine.

* * * * *